(12) United States Patent
De Lange et al.

(10) Patent No.: US 10,246,423 B2
(45) Date of Patent: Apr. 2, 2019

(54) PROCESS FOR PREPARING STATIN PRECURSOR

(71) Applicant: DSM Sinochem Pharmaceuticals Netherlands B.V., Delft (NL)

(72) Inventors: Ben De Lange, Echt (NL); Karin Henderika Maria Bessembinder, Echt (NL); Dennis Heemskerk, Echt (NL)

(73) Assignee: Centrient Pharmaceuticals Netherlands B.V. (NL)

( * ) Notice: Subject to any disclaimer, the term of this patent is extended or adjusted under 35 U.S.C. 154(b) by 0 days.

(21) Appl. No.: 15/545,682

(22) PCT Filed: Jan. 22, 2016

(86) PCT No.: PCT/EP2016/051312
§ 371 (c)(1),
(2) Date: Jul. 22, 2017

(87) PCT Pub. No.: WO2016/116589
PCT Pub. Date: Jul. 28, 2016

(65) Prior Publication Data
US 2018/0016241 A1    Jan. 18, 2018

(30) Foreign Application Priority Data

Jan. 23, 2015 (EP) ................................. 15152299

(51) Int. Cl.
*C07D 239/42* (2006.01)

(52) U.S. Cl.
CPC .................................. *C07D 239/42* (2013.01)

(58) Field of Classification Search
CPC .................................................... C07D 239/42
USPC .................................................. 544/330, 332
See application file for complete search history.

(56) References Cited

FOREIGN PATENT DOCUMENTS

WO     WO 03/006439      *  1/2003
WO     WO 2008/151510    * 12/2008

* cited by examiner

*Primary Examiner* — Deepak R Rao
(74) *Attorney, Agent, or Firm* — William D. Hare, Esq.; McNeely, Hare & War, LLP

(57) ABSTRACT

The present invention relates to a process for preparing a statin precursor, which process comprises a first reaction step, wherein a hydroxy-pyrimidine-carbonitrile is reacted with an organic sulfonyl halide to form the sulfonate-pyrimidine-carbonitrile; a second reaction step, wherein the sulfonate-pyrimidine-carbonitrile is reacted with N-methyl-methane sulfonamide to form a pyrimidinyl-sulfonamide; and optionally a third reaction step, wherein the pyrimidinyl-sulfonamide is reacted with a reducing agent. All steps are conducted in toluene as the main solvent.

20 Claims, No Drawings

PROCESS FOR PREPARING STATIN PRECURSOR

The invention is directed to a process for preparing a rosuvastatin precursor. In particular, the invention is directed to a process for preparing N-(5-cyano-4-(4-fluorophenyl)-6-isopropylpyrimidin-2-yl)-N-methylmethanesulfonamide and optionally subjecting this compound to a reduction step to form N-(4-(4-fluorophenyl)-5-formyl-6-isopropylpyrimidin-2-yl)-N-methylmethanesulfonamide.

Rosuvastatin, in particular rosuvastatin calcium, is a well-known HMG-CoA reductase inhibitor which is used for the treatment of hypercholesterolemia and to prevent cardiovascular disease. The compound according to formula (I):

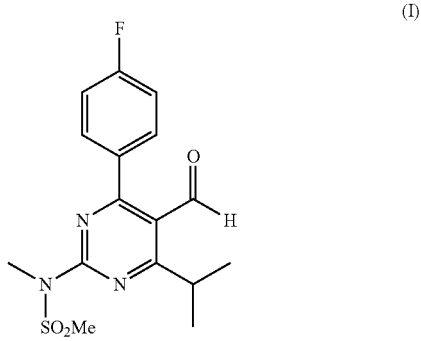 [SMILES: CC(C)c1nc(N(C)S(C)(=O)=O)nc(-c2ccc(F)cc2)c1C=O]

(I)

is a well-known precursor for preparing rosuvastatin. Different processes are known to prepare the compound of formula (I).

One such process is described in WO 2008/151510, wherein the compound of formula (I) is prepared from p-fluorobenzaldehyde, 4-methyl-3-oxopentanenitrile and urea. This process is represented in the reaction scheme below.

A disadvantage of the process of WO 2008/151510 is that each step is typically conducted in a separate solvent. Preferred solvents in the first step are methanol, ethanol and isopropanol. Preferred solvents in the second step are carboxylic acids, such as acetic acid, propionic acid and butyric acid. The most preferred solvents in the third step include ethyl acetate, butyl acetate and acetonitrile. Examples of solvents for the fourth step are benzene, toluene, xylene, dichloromethane, chloroform, tetrahydrofuran and dioxane. The use of different solvents in different reaction steps is generally not desirable in an industrial process, both in view of handling costs and recycling issues.

An object of the invention is to provide a process for preparing the compound of formula (I), wherein the same solvent is used in at least two subsequent steps.

In particular, it is an object of the invention to conduct the two reactions in step 3 and the reaction in step 4 of WO 2008/151510 in the same solvent. No solvent is described in WO2008/151510 that is considered suitable for each of the three reactions in step 3 and 4.

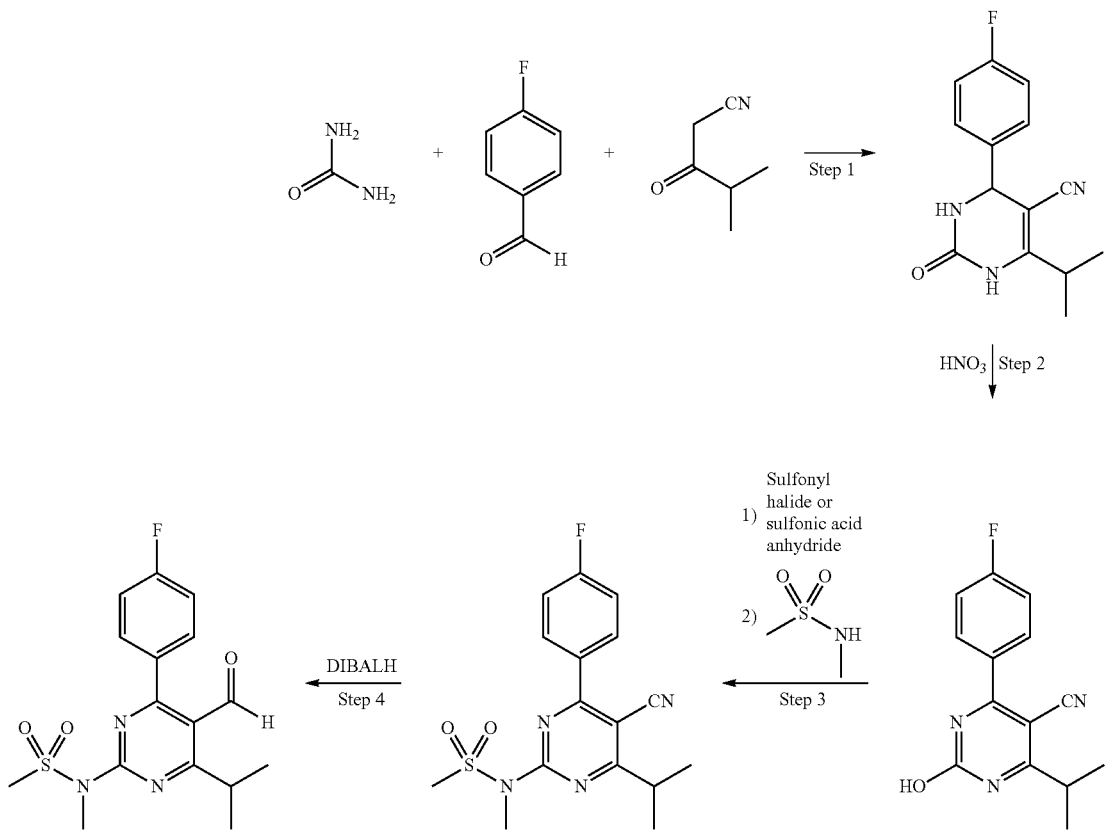

From an industrial perspective, it is highly desirable to use a single solvent for several process steps. In general for an efficient process, solvents need to be re-cycled in the process. Therefore handling of only one solvent is preferred to avoid several recovery plants. The use of toluene is highly preferred over, for example acetonitrile and n-butylacetate (which are suggested as preferred solvents for the third step in WO 2008/151510) due to the favourable azeotrope and low water solubility of toluene, which allows a very high recovery yield. Due to its miscibility with water, acetonitrile is far from preferred in this process as it would require an additional solvent for extraction and isolation.

Surprisingly, it was found that this reaction can be effectively carried out in toluene as both a base, like for example potassium carbonate as well as the substrate are nearly insoluble in toluene. This in contrast to, for example acetonitrile, which is a highly polar solvent wherein substrate and the base have a significant higher polarity. It is not obvious to choose for toluene in this type of chemistry. In general, more polar solvents like DMSO or NMP would be chosen by a person skilled in the art.

Finally, a single solvent like toluene allows integration of several steps, avoiding isolation and therefore increasing the overall yield.

Thus, the inventors found that the object could be met by using toluene as the solvent. Although the starting compound in step 3 (herein also referred to as the hydroxy-pyrimidine-carbonitrile) showed a low solubility in toluene, thus resulting in the reaction mixture being a suspension, the inventors found that the presence of undissolved hydroxy-pyrimidine-carbonitrile did not hinder the reaction as much as would be expected. In fact, the reaction resulted in an acceptable yield.

Accordingly, the invention is directed to a process for preparing a rosuvastatin precursor, comprising the steps of:
(a) providing a starting mixture comprising the compound of formula (II)

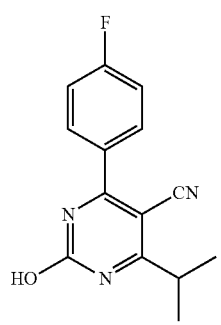

and toluene; and
(b) a first reaction step, wherein the starting mixture is contacted with an organic sulfonyl halide; and the resulting first reaction mixture is kept at a first temperature, thereby forming an intermediate mixture comprising the compound of formula (III)

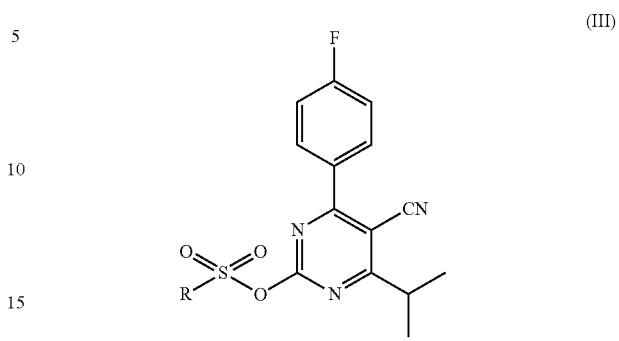

wherein R is an organic group; and
(c) a second reaction step, wherein the intermediate mixture is contacted with N-methylmethane sulfonamide; and the resulting second reaction mixture is kept at a second temperature, thereby forming a second mixture comprising the compound of formula (IV).

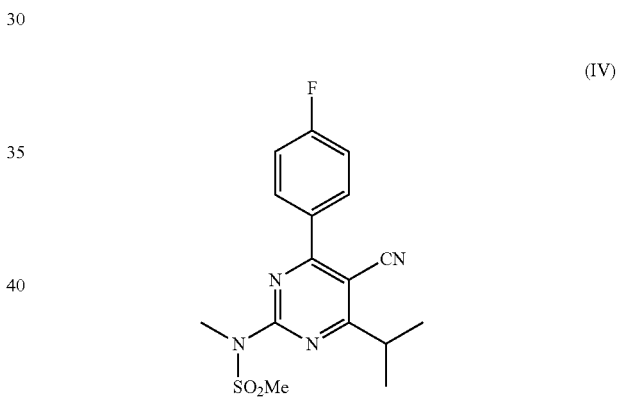

The compound of formula (IV) obtained in the second reaction step may subsequently be subjected to a reduction step in toluene, typically using diisobutylaluminium hydride (DIBALH) as the reducing agent. It is advantageous that the reduction step uses the same solvent as the first and second reaction steps. Besides the advantages in solvent recycling, this also allows for the possibility of integrating such steps and/or skipping isolation steps of intermediates obtained in such steps, for example those obtained in the second reaction step.

The inventors further found that when performing the step of reacting the hydroxy-pyrimidine-carbonitrile with an organic sulfonyl halide (first reaction step) and subsequently with N-methylmethane sulfonamide (second reaction step) in toluene, these reaction steps resulted in the formation of a dimer. Without wishing to be bound by any theory, the inventors expect that the following side-reaction takes place:

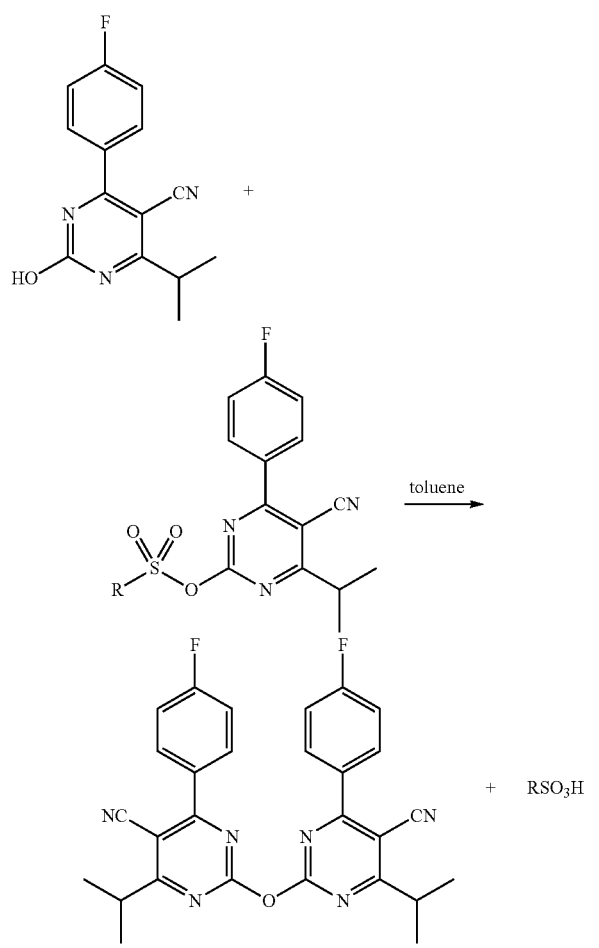

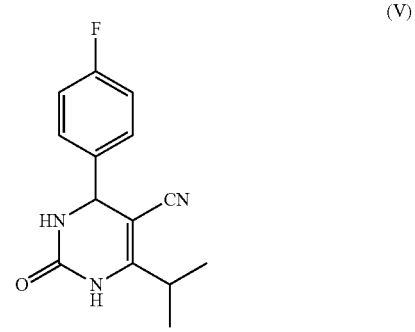 [SMILES: CC(C)C1=C(C#N)C(c2ccc(F)cc2)NC(=O)N1]

The inventors realized that in order to obtain a good yield in toluene, formation of the dimer should be prevented, or at least reduced. They found that this could be achieved by conducting the reaction at relatively low temperatures, preferably below 110° C. Furthermore, they found that when using a specific dosing protocol for contacting the N-methylmethane sulfonamide with the intermediate mixture, the formation of the dimer could be prevented even further. According to this dosing protocol, the intermediate mixture is added to a mixture of N-methylmethane sulfonamide in toluene over a period of time of at least one hour. These measures to reduce dimerization are discussed in more detail further below.

As used herein, the term "rosuvastatin precursor" will generally refer to the compound of formula (I). However, in case the process of the invention is conducted without the reduction step, the rosuvastatin precursor may also refer to the compound of formula (IV).

Unless noted otherwise, the term "mixture" as used herein typically refers to a solution (e.g. in case of the intermediate mixture and second reaction mixture). Exceptions are the starting mixture and the initial first reaction mixture, which are typically suspensions, as explicitly explained below. Furthermore, the term "mixture" as used herein typically refers to a mixture wherein the main solvent is toluene. This means that preferably at least 90 wt. %, more preferably at least 95 wt. %, even more preferably at least 99 wt. %, even more preferably at least 99.9 wt. % of the solvent present in the mixture is toluene.

The process of the invention is discussed in detail herein below. The process of the invention is primarily directed to three reaction steps. In the first reaction step, the hydroxy-pyrimidine-carbonitrile of formula (II) is reacted with an organic sulfonyl halide to form the sulfonate-pyrimidine-carbonitrile of formula (III), generally in the presence of a base. In the second reaction step, the sulfonate-pyrimidine-carbonitrile is reacted with N-methylmethane sulfonamide to form the pyrimidinyl-sulfonamide of formula (IV). In the third step (reduction step), the pyrimidinyl-sulfonamide of formula (IV) is reacted with a reducing agent to obtain the rosuvastatin precursor of formula (I).

According to the process of the invention, first a starting mixture is provided comprising the compound of formula (II). This compound is typically prepared by reacting p-fluorobenzaldehyde, 4-methyl-3-oxopentanenitrile and urea to form the compound of formula (V)

(V)

and subsequently oxidizing this compound to form the compound of formula (II). These reactions may for example be conducted by following the process as described in WO2008/151510.

Since the compound of formula (II) has a low solubility in toluene, the compound of formula (II) is typically suspended in the toluene in the starting mixture. The starting mixture is thus typically in the form of a suspension. Preferably, at least 95 wt. %, more preferably at least 99 wt. %, even more preferably at least 99.9 wt. % of the organic solvent present in the starting mixture is toluene. Most preferably, toluene is the only solvent present in the starting mixture. The use of a single solvent is desirable in view of handling costs and recycling issues, as well as the integration with other reaction steps. The starting mixture may comprise 1-30 wt. %, for example 5-20 wt. % of the compound of formula (II), based on the total weight of toluene present in the mixture. The same weight percentages may also apply to the reaction mixture after having contacted the organic sulfonyl halide. Typically, no significant amount of toluene is added during contacting of this compound.

In the first reaction step, the compound of formula (II) is reacted with an organic sulfonyl halide to form the compound of formula (III). An organic sulfonyl halide is a compound of the general formula R—SO$_2$X, wherein X is a halide and R is an organic group, typically having 1 up to 15 carbon atoms. The halide may be chloride, bromide, fluoride or iodide. The organic group may be a substituted or unsubstituted aromatic hydrocarbon (preferably phenyl or naphthyl), alkane (preferably methyl, ethyl, propyl or butyl) or cycloalkane. In case the organic group is substituted, the organic group may be substituted with one or more substituting groups, which are preferably selected from C1-C4 alkyl (preferably methyl), halide (e.g. Cl, Br, F, I) and nitro (NO$_2$). The definition of the R group given above for the organic sulfonyl halide also applies to the R group of the compound of formula (III).

Examples of suitable organic sulfonyl halides are methanesulfonyl chloride, ethanesulfonyl chloride, trifluoromethanesulfonyl chloride, methanesulfonyl bromide, benzenesulfonyl chloride, benzenesulfonyl bromide, p-toluenesulfonyl chloride, p-toluenesulfonyl bromide, p-toluenesulfonyl fluoride, 4-chlorobenzenesulfonyl chloride, 2-chlorobenzenesulfonyl chloride, 2-nitrobenzenesulfonyl chloride, 2-naphtalenesulfonyl chloride and 2,4,6-trimethylbenzenesulfonyl chloride. Good results have been obtained using organic sulfonyl chlorides. Preferably, p-toluenesulfonyl chloride (p-TsCl) is used as the organic sulfonyl chloride.

The starting mixture comprising the compound of formula (II) is first contacted with the organic sulfonyl halide to form the reaction mixture. This can be done by adding the organic sulfonyl halide to the starting mixture, for example during a period of time of 1-60 minutes.

The reaction mixture obtained after contacting is kept at a first temperature, thereby forming an intermediate mixture comprising the compound of formula (III). The first temperature is preferably a temperature of between 50° C. and 110° C., more preferably between 60° C. and 100° C., for example between 70 and 90° C. or between 75 and 85° C. The reaction mixture may be kept at the first temperature for an appropriate duration, for example for at least 1 hour, preferably for at least 2 hours, for example at least 3 hours.

The reaction between the compound of formula (II) and the organic sulfonyl halide is typically conducted in the presence of a base. The base may for example be selected from the group consisting of potassium carbonate, sodium carbonate, sodium hydroxide, potassium hydroxide, sodium methoxide, potassium methoxide, sodium tert-butoxide, potassium tert-butoxide, sodium tert amyl alcohol and potassium tert amyl alcohol. Good results have been achieved using an inorganic base. Preferably, the base is potassium carbonate. The molar amount of base used in the reaction may be at least equal, for example 1-5 times the molar amount of the compound of formula (II) present in the mixture. Preferably, the base is present in the starting mixture. Nevertheless, the base may also be contacted with the starting mixture, e.g. during or after contacting the starting mixture with the organic sulfonyl halide. This is typically achieved by simply adding the base to the starting mixture. Accordingly, the first reaction mixture will comprise the base.

After conducting the first reaction step, the resulting intermediate mixture is subjected to the second reaction step. Preferably, the compound of formula (III) is not isolated between the first and second reaction step. Rather, the compound of formula (III) is kept in solution in toluene in the intermediate mixture until it is reacted further in the second reaction step. Thus, the first and second reaction step may be conducted in the same reaction vessel.

In the second reaction step, the compound of formula (III) is reacted with N-methylmethane sulfonamide to form the compound of formula (IV).

The intermediate mixture comprising the compound of formula (III) is first contacted with N-methylmethane sulfonamide. The resulting reaction mixture (referred to as the 'second reaction mixture') is kept at a second temperature for an appropriate time to form a second mixture comprising the compound of formula (IV).

Contacting the intermediate mixture with N-methylmethane sulfonamide can be done by simply adding the N-methylmethane sulfonamide to the intermediate mixture, for example during a period of time of 1-180 minutes. To avoid the formation of dimers, the two reagents are preferably brought into contact with each other over a relatively long amount of time. For example, the N-methylmethane sulfonamide may be added (typically drop wise) to the intermediate mixture during a period of time of at least 1 hour, preferably at least 1.5 hours.

The inventors found that dimerization may in particular be avoided when using a specific dosing protocol, wherein the intermediate mixture is brought in contact with the N-methylmethane sulfonamide in a very specific manner. According to this dosing protocol, the intermediate mixture is added (typically drop wise) to a mixture comprising N-methylmethane sulfonamide, toluene and optionally a base (hereinafter referred to as the sulfonamide mixture). Contacting the reagents in this way was found to result in a significant reduction in dimer formation. The intermediate mixture is preferably added slowly, over a relatively long period of time, in order to reduce the occurrence of dimerization. Accordingly, the intermediate mixture is added to the sulfonamide mixture over a period of time of at least 0.5 hour, preferably at least 1 hour, more preferably at least 2 hours, even more preferably at least 2.5 hours. The sulfonamide mixture may comprise 1-60 wt. %, preferably 10-50 wt. % N-methylmethane sulfonamide, relative to the total weight of toluene in the sulfonamide mixture. The sulfonamide mixture may have a temperature of between 50° C. and 110° C., preferably between 60° C. and 100° C., for example between 70° C. and 90° C. or between 75° C. and 85° C. during contacting. The intermediate mixture may have a temperature in this same range. The base that may be present in the sulfonamide mixture is typically the same type of base that is typically present in the reaction between the compound of formula (III) and N-methylmethane sulfonamide. The molar amount of N-methylmethane sulfonamide present in the sulfonamide mixture may be at least 0.9 times, preferably 1.0 to 1.3 times the molar amount of the compound of formula (III) present in the intermediate mixture The reaction mixture obtained after having contacted the different reagents is kept at a second temperature for an appropriate duration, preferably for at least 1 hour, more preferably at least 2 hours, for example at least 3 hours. The second temperature is preferably a temperature of between 50° C. and 110° C., more preferably between 60° C. and 100° C., for example between 70° C. and 90° C. or between 75° C. and 85° C. Thus, a mixture is obtained comprising the compound of formula (IV), which mixture is herein referred to as the second mixture.

The reaction between the compound of formula (III) and N-methylmethane sulfonamide is typically conducted in the presence of a base. The base may for example be selected from the group consisting of potassium carbonate, sodium carbonate, sodium hydroxide, potassium hydroxide, sodium methoxide, potassium methoxide, sodium tert-butoxide, potassium tert-butoxide, sodium tert amyl alcohol and potassium tert amyl alcohol. Good results have been obtained using an inorganic base. Preferably, the base is potassium carbonate. The molar amount of base used in the reaction may be at least equal, for example 1-5 times the molar amount of the compound of formula (III) present in the mixture. This base may be the same or a different base than the one already present in the first reaction step. The base may already be present in the intermediate mixture. Alternatively, or in addition, additional base may be added for the second reaction step. In this case, the intermediate mixture may be contacted with additional base, either before, during or after contacting with the organic sulfonyl halide. The additional base may for example be contacted with the intermediate mixture by simply adding the base to the intermediate mixture. This is typically done before contacting the intermediate mixture with the N-methylmethane sulfonamide. In case of the specific dosing protocol described above, the base will preferably be present in the mixture of N-methylmethane sulfonamide and toluene.

After forming the compound of formula (IV) in the second reaction step, the second mixture may be washed with toluene and/or water.

The compound of formula (IV) may then be isolated, for example by concentrating the second mixture and subsequently crystallizing the compound of formula (IV), e.g. by cooling the reaction mixture. Alternatively, the compound of formula (IV) is kept in dissolved form in the (optionally washed) second mixture.

In the third step (also referred to as the reduction step), the compound of formula (IV) is reacted with a reducing agent to form the compound of formula (I). The reducing agent is preferably DIBALH. The inventors found that very good results could be obtained for the reduction in toluene using this specific reducing agent.

The inventors further found that a relatively small amount of DIBALH is already sufficient to obtain an efficient and complete reduction. The molar amount of DIBALH used in the reaction may be 1.0 to 1.5 times, preferably 1.1 to 1.3 times the molar amount of the compound of formula (IV). In other words, only 1.0 to 1.5 molar equivalents, preferably 1.1 to 1.3 equivalents of DIBALH are preferably used per equivalent of the compound of formula (IV) for the reduction.

The mixture of the compound of formula (IV) in toluene may comprise 5-50, preferably 10-40 wt. % of the compound of formula (IV), based on the total weight of toluene in the mixture. The mixture of the compound of formula (IV) in toluene may be the second mixture obtained in the second reaction step. Alternatively, in case the compound of formula (IV) was isolated from the second mixture, the mixture may instead be prepared from dissolving the compound of formula (IV) isolated in the second reaction step in toluene. Due to the low solubility of the compound of formula (IV) in toluene, the mixture may be a suspension.

The reduction reaction according to the process of the invention may be conducted by contacting a mixture of the compound of formula (IV) in toluene with a reducing agent, in particular with diisobutylaluminium hydride (DIBALH). DIBALH is preferably brought into contact with the mixture in the form of a solution in toluene. Good results were obtained using a DIBALH in toluene solution having a concentration of 10-40, preferably 20-30 wt. % DIBALH, based on the total weight of toluene in the solution.

The mixture of the compound of formula (IV) in toluene and the DIBALH solution in toluene are preferably brought into contact with each other at a temperature below 20° C., preferably a temperature of −50 to 10° C., more preferably of −20 to 0° C. This is typically done by adding the solution (typically drop wise) to the mixture over an amount of time of at least 15 minutes, preferably at least 0.5 hours.

After contacting, the reaction mixture is kept at a temperature below 20° C., preferably a temperature of −50 to 10° C., more preferably of −20 to 0° C. for an appropriate amount of time, typically 10-120 minutes. The resulting product mixture comprises the compound of formula (I).

Subsequently, the product mixture may be quenched, for example by adding it to hydrochloric acid while keeping the temperature below 20° C. The thus quenched product mixture is then heated to a temperature of 50-100° C., after which the layers organic (toluene) layer may be separated from the aqueous layer. The compound of formula (I) may be isolated from the organic layer by concentration and crystallization, e.g. by cooling crystallization.

The invention is illustrated by the following experimental Examples.

EXAMPLES

Example 1A: Pyrimidine-Sulfonamide Formation in Toluene

This Example shows the preparation of N-(5-cyano-4-(4-fluorophenyl)-6-isopropylpyrimidin-2-yl)-N-methylmethanesulfonamide from 4-(4-fluorophenyl)-2-hydroxy-6-isopropylpyrimidin-5-carbonitrile in toluene. The reaction mechanism is as follows.

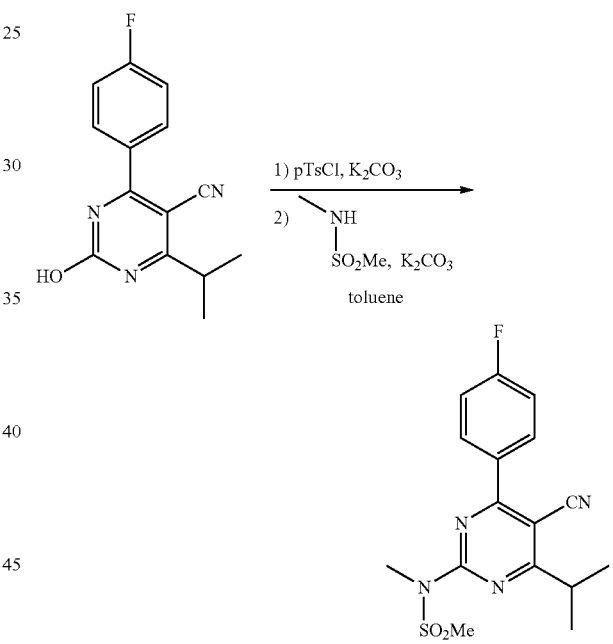

A reactor is charged with toluene (90 mL), (4-fluorophenyl)-2-hydroxy-6-isopropyl pyrimidine-5-carbonitrile (10 g, 38.9 mmol) and $K_2CO_3$ (17.2 g, 124.4 mmol). Then pTsCl (9.6 g, 50.5 mmol, para-toluene sulfonylchloride) is added under stirring in 30 min. The reaction mixture is heated to 100° C. and kept at this temperature for 3 h. After cooling to 80° C., NMSA (6.4 g, 58.3 mmol, N-methylmethane sulfonamide) is added, followed by stirring at 80° C. for 7 h. The reaction mixture contains approximately 10% of dimer during this step. Toluene (140 mL) is added followed by careful addition of water (170 mL). The reaction mixture is heated to 90° C. After stirring for 30 min, the phases are separated. The organic layer is concentrated under reduced pressure until crystallization of the product starts. Then distillation is stopped and the slurry is heated to 100° C. until a clear solution is obtained. If required a small amount of toluene is added. The reaction mixture is cooled in 6 h to 20° C. and stirred for 16 h. The precipitated solid is isolated by filtration and washed with toluene (3×8 mL). After drying, N-(5-cyano-4-(4-fluorophenyl)-6-isopropylpyrimidin-2-yl)-N-methylmethane sulfonamide is obtained as a white solid (9.5 g, yield 70%). $^1$H NMR (300 MHz, CDCl$_3$) δ1.38-1.40 (d, 6H, J=6.9 Hz), 3.40-3.43 (m, 1H), 3.53 (s, 3H), 3.55-3.65 (m, 1H), 3.64 (s, 3H), 7.21-7.27 (m, 2H), 8.08-8.13 (m, 2H).

Example 1B: Pyrimidine-Sulfonamide Formation Using Dosing Protocol

This Example shows the preparation of N-(5-cyano-4-(4-fluorophenyl)-6-isopropylpyrimidin-2-yl)-N-methylmethanesulfonamide from 4-(4-fluorophenyl)-2-hydroxy-6-isopropylpyrimidin-5-carbonitrile in toluene, wherein a specific dosing protocol is used for adding the N-methylmethane sulfonamide. The reaction mechanism is as follows.

protocol). As a result, the yield of the pyrimidine-sulfonamide was increased from 70% in Example 4A to 78% in Example 4B.

Example 1C: Pyrimidine-Sulfonamide Isolation Via Direct Filtration

This Example shows the preparation of N-(5-cyano-4-(4-fluorophenyl)-6-isopropylpyrimidin-2-yl)-N-methylmethanesulfonamide from 4-(4-fluorophenyl)-2-hydroxy-6-isopropylpyrimidin-5-carbonitrile in toluene. The formed pyrimidine-sulfonamide was isolated directly from the reaction mixture using cooling filtration (as opposed to conducting an extraction step with water prior to filtration, as was done in Examples 1A and 1B). The reaction mechanism is as follows.

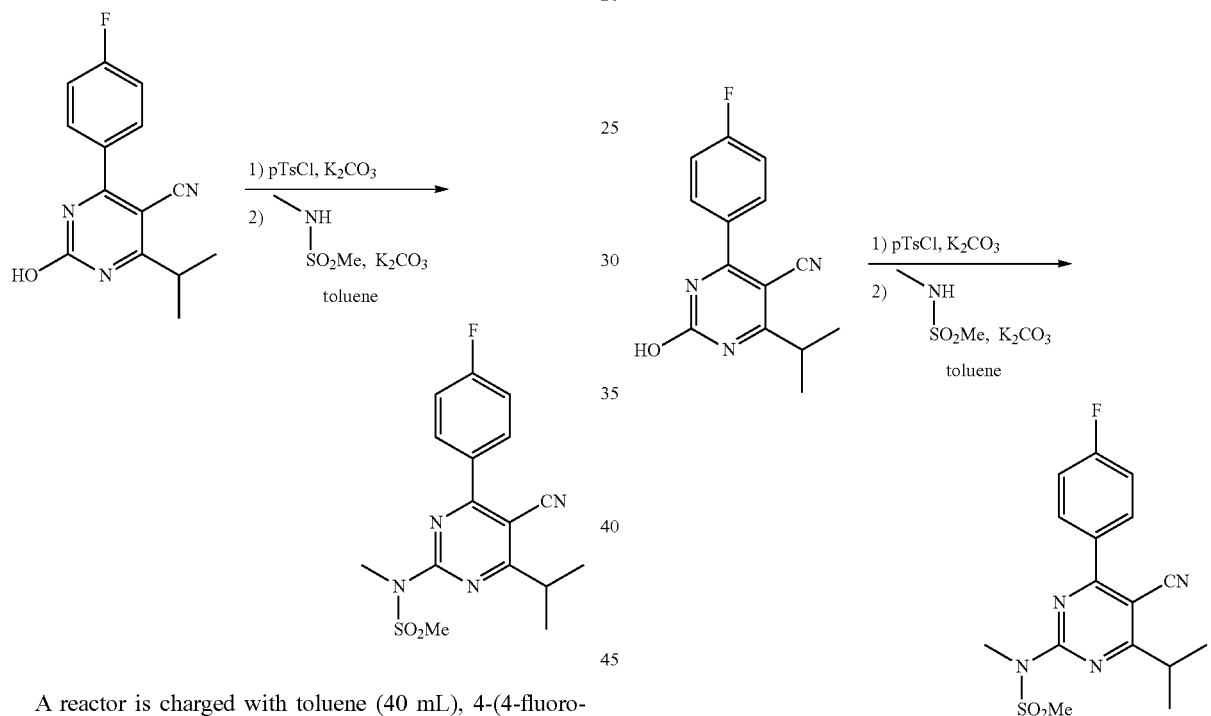

A reactor is charged with toluene (40 mL), 4-(4-fluorophenyl)-2-hydroxy-6-isopropyl pyrimidine-5-carbonitrile (5.0 g, 19.4 mmol) and K$_2$CO$_3$ (4.0 g, 29.2 mmol). Then pTsCl (4.8 g, 25.3 mmol, para-toluene sulfonylchloride) is added under stirring in 15 min. The reaction mixture is heated to 100° C. and kept at this temperature for 2 h, then cooled to 80° C. (step A). In another reactor, a mixture of NMSA (3.2 g, 29.1 mmol N-methylmethane sulfonamide), K$_2$CO$_3$ (4.8 g, 33.1 mmol) in toluene (20 mL) was prepared and heated to 80° C. (step B). The mass of step A is added 3 h at 80° C. to the reaction mixture of step B. Thereafter, the total mass was stirred for another 4 h at 80° C. The reaction mixture contains approximately 5% of dimer during this step. The extraction and isolation procedure was done as described in example 4A to give N-(5-cyano-4-(4-fluorophenyl)-6-isopropylpyrimidin-2-yl)-N-methylmethane sulfon amide as a white solid (5.3 g, yield 78%).

It can be concluded from Examples 4A and 4B that dimer formation can be reduced by using a dosing protocol. Only half the amount of dimers was formed in Example 4B (dosing protocol) compared to Example 4A (no dosing A reactor is charged with toluene (75 mL), (4-fluorophenyl)-2-hydroxy-6-isopropyl pyrimidine-5-carbonitrile (10 g, 38.9 mmol) and K$_2$CO$_3$ (6.4 g, 46.1 mmol). Then pTsCl is added (8.1 g, 42.5 mmol, para-toluenesulfonylchloride) under stirring in 30 min. The reaction mixture is heated to 110° C. and kept at this temperature for 3 h. After cooling to 100° C., K$_2$CO$_3$ (7.4 g, 53.3 mmol) and NMSA (5.5 g, 50.4 mmol, N-methylmethane sulfonamide) are added. The reaction mixture is heated to 110° C., kept at this temperature for 3 h, and then cooled to 20° C. The solids are isolated by filtration and washed with toluene (2×10 mL). This solid was suspended in water (50 mL) and stirred for 1 h at 20° C. The solid is isolated by filtration, washed with water (2×20 mL). After drying, N-(5-cyano-4-(4-fluorophenyl)-6-isopropylpyrimidin-2-yl)-N-methylmethane sulfon amide is obtained as a white solid (9.5 g, yield 70%).

Example 2: Pyrimidine-Sulfonamide Reduction in Toluene

This Example shows the preparation of N-(4-(4-fluorophenyl)-5-formyl-6-isopropylpyrimidin-2-yl)-N-methylmethanesulfonamide from N-(5-cyano-4-(4-fluorophenyl)-6-isopropylpyrimidin-2-yl)-N-methylmethanesulfonamide using diisobutylaluminium hydride (DiBALH) as a reducing agent. The reaction mechanism is as follows.

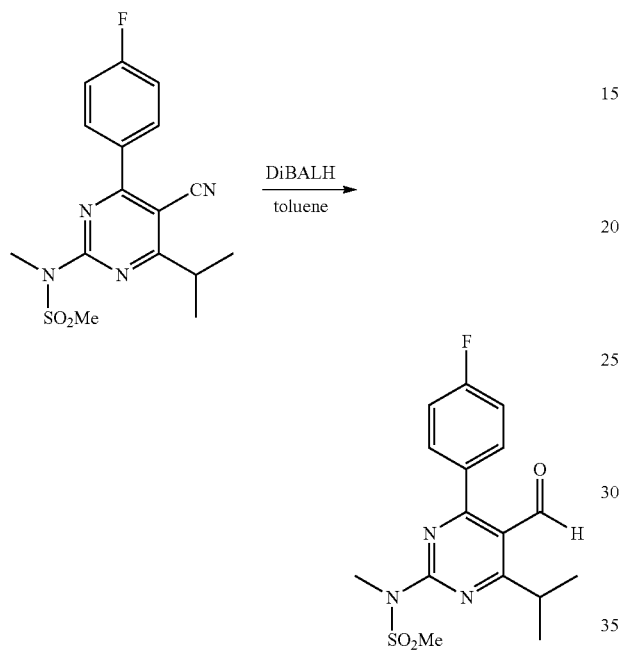

A reactor is charged with toluene (50 mL) and N-(5-cyano-4-(4-fluorophenyl)-6-isopropylpyrimidin-2-yl)-N-methylmethanesulfonamide (6.0 g, 17.2 mmol) and cooled to −5° C. To the stirred white suspension is dosed in 1 h a solution of DiBALH in toluene (15.1 mL of a 25 w/w % solution of diisobutylaluminum hydride in toluene, 22.2 mmol) keeping the temperature at ~−5° C. Stirring is continued for 1 h at −5° C. Then this reaction mixture is added to 4 M aqueous HCl (50 mL) keeping the temperature <20° C. After the transfer is completed, toluene (10 mL) is used to transfer the last part of the reaction mixture into the aqueous HCl. The quenched reaction mixture is heated to 85° C. The layers are separated. The organic layer is concentrated under vacuum until precipitation occurs. Then distillation is stopped and the toluene is heated to 110° C. The clear solution is cooled in 5 h to 20° C. and stirred for 16 h. The precipitated solid is isolated by filtration, washed with toluene (3×6 mL). After drying, N-(4-(4-fluorophenyl)-5-formyl-6-isopropylpyrimidin-2-yl)-N-methylmethanesulfonamide is obtained as a white solid (4.9 g, yield 81%). $^1$H NMR (300 MHz, CDCl$_3$) δ1.32-1.34 (d, 6H, J=7.0 Hz), 3.55 (s, 3H), 3.64 (s, 3H), 3.97-4.06 (m, 1H), 7.20-7.27 (m, 2H), 7.61-7.66 (m, 2H), 9.90 (s, 1H).

The invention claimed is:
1. A process for preparing the compound of formula (IV), the process comprising the steps of:
(a) providing a starting mixture comprising the compound of formula (II) and toluene

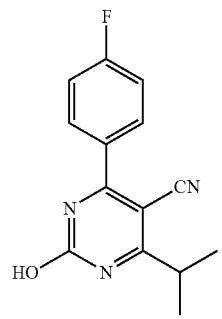

(b) a first reaction step, wherein the starting mixture is contacted with an organic sulfonyl halide and the resulting first reaction mixture is kept at a first temperature of below 110° C., thereby forming an intermediate mixture comprising the compound of formula (III)

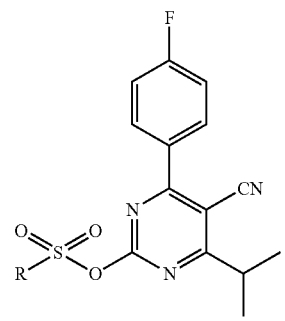

wherein R is an organic group having from 1 to 15 carbons; and
(c) a second reaction step, wherein the intermediate mixture is contacted with N-methylmethane sulfonamide and the resulting second reaction mixture is kept at a second temperature, thereby forming a second mixture comprising the compound of formula (IV)

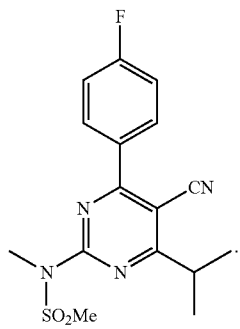

2. The process according to claim 1 wherein toluene is present in steps (a), (b) and (c).
3. The process according to claim 1, further comprising a reduction step, wherein the compound of formula (IV) obtained in the second reaction step is reacted with a reducing agent in toluene to form the compound of formula (I)

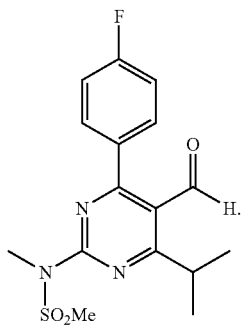

(I)

4. The process according to claim 1, wherein the first and second temperature are independently chosen to lie in the range of 50 to 110° C.

5. The process according to claim 1, wherein the intermediate mixture is contacted with N-methylmethane sulfonamide by adding the intermediate mixture to a sulfonamide mixture comprising N-methylmethane sulfonamide in toluene.

6. The process according to claim 5, wherein the intermediate mixture is added to the mixture comprising N-methylmethane sulfonamide over a period of at least 1 hour.

7. The process according to claim 5, wherein the mixture comprising N-methylmethane sulfonamide further comprises a base.

8. The process according to claim 5, wherein the sulfonamide mixture comprises 1-60 wt. % N-methylmethane sulfonamide, relative to the total weight of toluene in the sulfonamide mixture.

9. The process according to claim 1, wherein the organic sulfonyl halide is selected from the group consisting of methanesulfonyl chloride, ethanesulfonyl chloride, trifluoromethanesulfonyl chloride, methanesulfonyl bromide, benzenesulfonyl chloride, benzenesulfonyl bromide, p-toluenesulfonyl chloride, p-toluenesulfonyl bromide, p-toluenesulfonyl fluoride, 4-chlorobenzenesulfonyl chloride, 2-chlorobenzenesulfonyl chloride, 2-nitrobenzenesulfonyl chloride, 2-naphtalenesulfonyl chloride and 2,4,6-trimethylbenzenesulfonyl chloride.

10. The process according to claim 1, wherein the first and second reaction steps are conducted in the presence of a base selected from the group consisting of potassium carbonate, sodium carbonate, sodium hydroxide, potassium hydroxide, sodium methoxide, potassium methoxide, sodium tert-butoxide, potassium tert-butoxide, sodium tert-amyl alcohol and potassium tert-amyl alcohol.

11. The process according to claim 1, wherein R having from 1 to 15 carbons is an aromatic hydrocarbon, alkane or cycloalkane, optionally substituted with one or more of C1-C4 alkyl, halide or nitro.

12. The process according to claim 1, wherein at least 95 wt. % of the organic solvent present in the starting mixture, first reaction mixture and second reaction mixture is toluene.

13. The process according to claim 1, wherein the starting mixture is a suspension of the compound of formula (II) in toluene.

14. The process according to claim 3, wherein the reducing agent is diisobutylaluminium hydride.

15. The process according to claim 14, wherein the reduction reaction is conducted by contacting a mixture of the compound of formula (IV) in toluene with a solution of DIBALH in toluene at a temperature below 20° C. and keeping the resulting mixture at said temperature below 20° C. for an amount of time.

16. The process according to claim 15, wherein the amount of time that the resulting mixture is kept at a temperature below 20° C. is about 10-120 minutes.

17. The process according to claim 1, wherein in the starting mixture at least 90% of any solvent present is toluene.

18. The process according to claim 1, wherein in the first reaction mixture at least 90% of any solvent present is toluene.

19. The process according to claim 1, wherein in the intermediate mixture at least 90% of any solvent present is toluene.

20. The process according to claim 1, wherein in the second reaction mixture at least 90% of any solvent present is toluene.

* * * * *